US011963759B2

(12) United States Patent
Osawa et al.

(10) Patent No.: US 11,963,759 B2
(45) Date of Patent: Apr. 23, 2024

(54) STATE DETERMINATION DEVICE, STATE DETERMINATION METHOD, AND RECORDING MEDIUM

(71) Applicant: Mitsubishi Electric Corporation, Tokyo (JP)

(72) Inventors: Shunya Osawa, Tokyo (JP); Takahiro Otsuka, Tokyo (JP)

(73) Assignee: Mitsubishi Electric Corporation, Tokyo (JP)

( * ) Notice: Subject to any disclaimer, the term of this patent is extended or adjusted under 35 U.S.C. 154(b) by 438 days.

(21) Appl. No.: 17/326,795

(22) Filed: May 21, 2021

(65) Prior Publication Data

US 2021/0271865 A1  Sep. 2, 2021

Related U.S. Application Data

(63) Continuation of application No. PCT/JP2018/045595, filed on Dec. 12, 2018.

(51) Int. Cl.
*A61B 5/11* (2006.01)
*A61B 5/00* (2006.01)
(Continued)

(52) U.S. Cl.
CPC .......... *A61B 5/1128* (2013.01); *A61B 5/1123* (2013.01); *A61B 5/4809* (2013.01); *G06V 40/171* (2022.01); *G06V 40/20* (2022.01)

(58) Field of Classification Search
CPC ... A61B 5/1128; A61B 5/1123; A61B 5/4809; A61B 5/1104; A61B 5/163; A61B 5/18; A61B 5/4845; G06V 40/171; G06V 40/20
See application file for complete search history.

(56) References Cited

U.S. PATENT DOCUMENTS

2005/0024212 A1* 2/2005 Hultzsch .............. B60K 28/066
340/576
2016/0110586 A1 4/2016 Hayasaka
(Continued)

FOREIGN PATENT DOCUMENTS

JP 11-339200 A 12/1999
JP 2008-212298 A 9/2008
(Continued)

OTHER PUBLICATIONS

Dalal et al., "Histograms of Oriented Gradients for Human Detection", International Conference on Computer Vision & Pattern Recognition (CVPR '05), Jun. 2005, San Diego, United States, pp. 886-893.
(Continued)

*Primary Examiner* — Xuemei G Chen
(74) *Attorney, Agent, or Firm* — Birch, Stewart, Kolasch & Birch, LLP

(57) ABSTRACT

A state determination device includes: an extraction unit that extracts a face region representing a region corresponding to a face from each of a plurality of frames successively obtained by capturing images of a user's face, extracts face feature points representing parts of the face from the face region, calculates a face feature value extraction region as a region where a change occurs in the face region when the user is in an unawakened state based on the face feature points, and extracts a face feature value as a feature value from the face feature value extraction region;
a state determination unit that determines whether the user is in the unawakened state or not based on the face feature value in each of the plurality of frames and previously generated determination information; and an output unit that outputs a determination result.

15 Claims, 16 Drawing Sheets

(51) Int. Cl.
  *G06V 40/16* (2022.01)
  *G06V 40/20* (2022.01)

(56) References Cited

U.S. PATENT DOCUMENTS

| | | | |
|---|---|---|---|
| 2016/0272217 A1* | 9/2016 | Kim | G06V 40/166 |
| 2018/0012090 A1* | 1/2018 | Herbst | G06V 40/20 |
| 2018/0194365 A1* | 7/2018 | Bae | B60W 50/0098 |
| 2018/0330177 A1* | 11/2018 | Ryu | B60Q 9/00 |
| 2019/0065873 A1* | 2/2019 | Wang | G06V 40/168 |
| 2019/0197329 A1* | 6/2019 | Aoyagi | G06V 40/20 |
| 2019/0279009 A1* | 9/2019 | Srirangam Narashiman | G06T 7/248 |
| 2019/0294129 A1* | 9/2019 | Muta | G05B 15/02 |
| 2019/0311014 A1* | 10/2019 | Sugawara | G01C 21/3617 |
| 2019/0320890 A1* | 10/2019 | Tahara | G06V 10/443 |
| 2019/0370578 A1* | 12/2019 | Meng | B60W 50/14 |
| 2020/0198649 A1* | 6/2020 | Emura | G05B 13/0265 |
| 2020/0247422 A1* | 8/2020 | Yoshida | A61M 21/00 |
| 2020/0322527 A1* | 10/2020 | Orikasa | H04N 7/18 |
| 2020/0359954 A1* | 11/2020 | Sunagawa | A61B 5/162 |
| 2021/0129748 A1* | 5/2021 | Tamrakar | G06F 3/167 |
| 2021/0341166 A1* | 11/2021 | Emoto | F24F 11/80 |

FOREIGN PATENT DOCUMENTS

| | | |
|---|---|---|
| JP | 2012-221061 A | 11/2012 |
| JP | 2016-81212 A | 5/2016 |
| JP | 2017-162409 A | 9/2017 |
| JP | 2017194772 A * | 10/2017 |

OTHER PUBLICATIONS

Viola et al., "Robust Real-Time Face Detection", International Journal of Computer Vision, 2004, vol. 57, No. 2, pp. 137-154.
Wiskott et al., "Face Recognition by Elastic Bunch Graph Matching", IR-INI 96-08, Apr. 1996, total 22 pages.

* cited by examiner

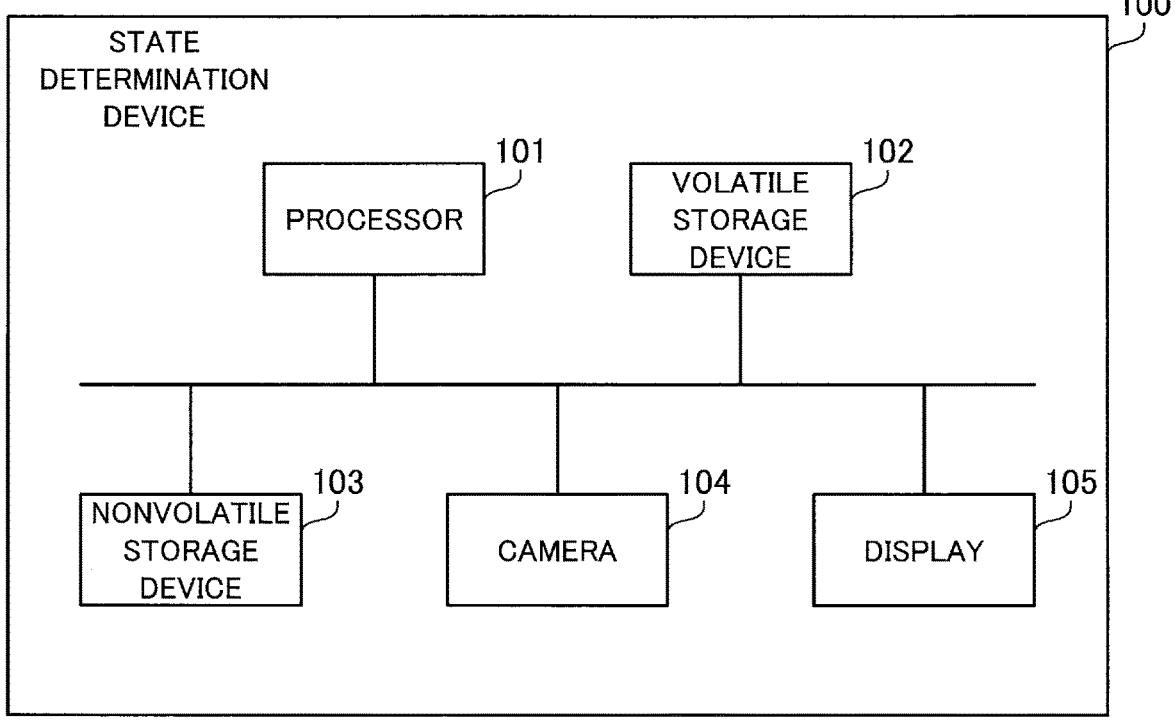

EXAMPLE OF CALCULATION OF GLABELLA REGION

EXAMPLE OF CALCULATION OF MOUTH REGION

FIG. 5

| FACE FEATURE VALUE TABLE | | 181a |
|---|---|---|
| FEATURE VALUE | VALUE | |
| V1 | 110 | |
| V2 | 30 | |
| V3 | 60 | |
| ... | ... | |

FIG. 6

| UNAWAKENEDNESS LEVEL | STATE DETERMINATION MODEL TABLE | | | 182a |
|---|---|---|---|---|
| | THE NUMBER OF TIMES OF WRINKLING GLABELLA IN 5 MINUTES (c) | THE NUMBER OF TIMES OF LICKING LIPS IN 5 MINUTES (d) | THE NUMBER OF TIMES OF YAWNING IN 5 MINUTES (e) | |
| Lv. 0 | 0 | 0 | 0 | |
| Lv. 1 | $0 < c \leq 1$ | $0 < d \leq 1$ | $0 < e \leq 1$ | |
| Lv. 2 | $1 < c \leq 2$ | $1 < d \leq 2$ | $1 < e \leq 2$ | |
| Lv. 3 | $2 < c \leq 3$ | $2 < d \leq 3$ | $2 < e \leq 3$ | |
| Lv. 4 | $3 < c \leq 4$ | $3 < d \leq 4$ | $3 < e \leq 4$ | |
| Lv. 5 | $4 < c$ | $4 < d$ | $4 < e$ | |

| THE NUMBER OF TIMES OF WRINKLING GLABELLA IN 5 MINUTES (c) | THE NUMBER OF TIMES OF LICKING LIPS IN 5 MINUTES (d) | THE NUMBER OF TIMES OF YAWNING IN 5 MINUTES (e) |
|---|---|---|
| Lv. 2 | Lv. 4 | Lv. 3 |

| AVERAGE FACE FEATURE POINT MODEL TABLE ||
|---|---|
| FEATURE POINT | AVERAGE COORDINATES |
| LEFT EYEBROW OUTER END | (100 , 100) |
| LEFT EYEBROW INNER END | (200 , 100) |
| LEFT EYE OUTER END | (300 , 100) |
| LEFT EYE INNER END | (400 , 100) |
| NOSE CENTER | (500 , 100) |
| MOUTH LEFT END | (600 , 100) |
| ... | ... |

FIG. 16(A) NORMAL CONDITION
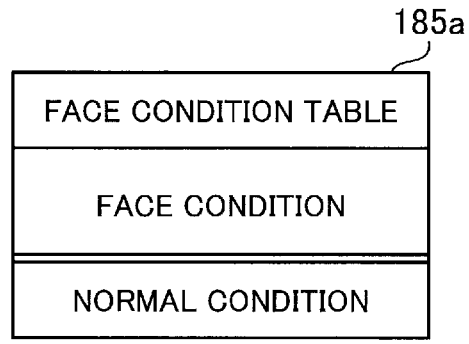
FIG. 16(B) WEARING MASK
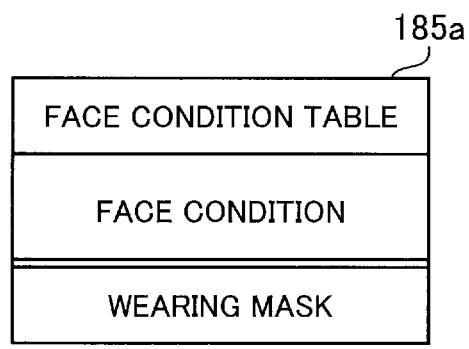
FIG. 16(C) LIGHT APPLIED FROM LEFT
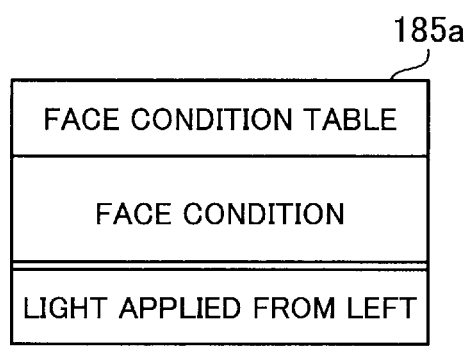

FIG. 17

| EXTRACTION REGION DETERMINATION MODEL TABLE | |
|---|---|
| FACE CONDITION | FACE FEATURE VALUE EXTRACTION REGION |
| NORMAL CONDITION | GLABELLA, MOUTH, CHEEK |
| WEARING SUNGLASSES | MOUTH, CHEEK |
| WEARING MASK | GLABELLA |
| LIGHT APPLIED FROM LEFT | GLABELLA, MOUTH, RIGHT CHEEK |
| ... | ... |

STATE DETERMINATION DEVICE, STATE DETERMINATION METHOD, AND RECORDING MEDIUM

CROSS-REFERENCE TO RELATED APPLICATION

This application is a continuation application of International Application No. PCT/JP2018/045595 having an international filing date of Dec. 12, 2018.

BACKGROUND OF THE INVENTION

1. Field of the Invention

The present invention relates to a state determination device, a state determination method and a recording medium storing a program.

2. Description of the Related Art

There are cases where a person falls into an unawakened state. The unawakened state is, for example, a dozing state, a state of dozing off due to drinking, or the like.

Meanwhile, in order to prevent accidents, development is being advanced on a technology for making a determination of the unawakened state of a person in a vehicle or a factory. For example, a feature value that changes when the person is in the unawakened state is extracted from heartbeat, brain waves, blinking or the like. Subsequently, the feature value and a threshold value are compared with each other. The determination of the unawakened state is made based on the result of the comparison. As above, the determination of the unawakened state can be made based on a biological signal such as the heartbeat. However, in this determination method, a sensor is attached to the person. Therefore, this determination method gives the person a feeling of troublesomeness. Further, this determination method cannot be used when the sensor is not attached to the person. Furthermore, this determination method requires a lot of cost since the sensor is used.

Here, a technology for detecting the dozing state has been proposed (see Patent Reference 1). For example, a drowsy driving detection device described in the Patent Reference 1 detects the dozing state of the driver by using the frequency of blinking. Further, there has been proposed a technology for making a determination of a sleepy state of a driver (see Patent Reference 2). For example, a sleepiness determination device described in the Patent Reference 2 makes the determination of the sleepy state by using the frequency of blinking.

Patent Reference 1: Japanese Patent Application Publication No. 1999-339200
Patent Reference 2: Japanese Patent Application Publication No. 2008-212298
Non-patent Reference 1: Paul Viola, Michael J Jones "Robust Real-Time Face Detection", International Journal of Computer Vision 57(2), 2004
Non-patent Reference 2: Laurenz Wiskott, Jean-Marc Fellous, Norbert Kruger, Christoph von der Malsburg "Face Recognition by Elastic Bunch Graph Matching", 1996
Non-patent Reference 3: Navneet Dalal and Bill Triggs "Histograms of Oriented Gradients for Human Detection"

The technologies of the Patent References 1 and 2 employ the blinking frequency. However, there are great individual differences in the blinking frequency. For example, in cases where the blinking frequency of a person when the person is awake is very high, it is difficult to determine whether the person is in the unawakened state or not by using the technologies of the Patent References 1 and 2.

Therefore, how to make the determination of the unawakened state with high accuracy is the problem.

SUMMARY OF THE INVENTION

The object of the present invention is to make the determination of the unawakened state with high accuracy.

A state determination device according to an aspect of the present invention is provided. The state determination device includes: an extraction unit that extracts a face region representing a region corresponding to a face from each of a plurality of frames successively obtained by capturing images of a user's face, extracts face feature points representing parts of the face from the face region, calculates a face feature value extraction region as a region where a change occurs in the face region when the user is in an unawakened state based on the face feature points, and extracts a face feature value as a feature value from the face feature value extraction region; a state determination unit that determines whether the user is in the unawakened state or not based on the face feature value in each of the plurality of frames and previously generated determination information; and an output unit that outputs a determination result.

According to the present invention, the determination of the unawakened state can be made with high accuracy.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIG. 2 is a diagram showing a configuration of hardware included in the state determination device in the first embodiment;

FIG. 3 is a diagram showing an example of a face feature point table in the first embodiment;

FIG. 5 is a diagram showing an example of a face feature value table in the first embodiment;

FIG. 6 is a diagram showing an example of a state determination model table in the first embodiment;

FIG. 15 is a diagram showing an example of an average face feature point model table in the second embodiment;

FIGS. 16(A) to 16(C) are diagrams showing examples of a face condition table;

FIG. 17 is a diagram showing an example of an extraction region determination model table in the second embodiment;

DETAILED DESCRIPTION OF THE INVENTION

Embodiments will be described below with reference to the drawings. The following embodiments are just examples and a variety of modifications are possible within the scope of the present invention.

First Embodiment

Figure 1:
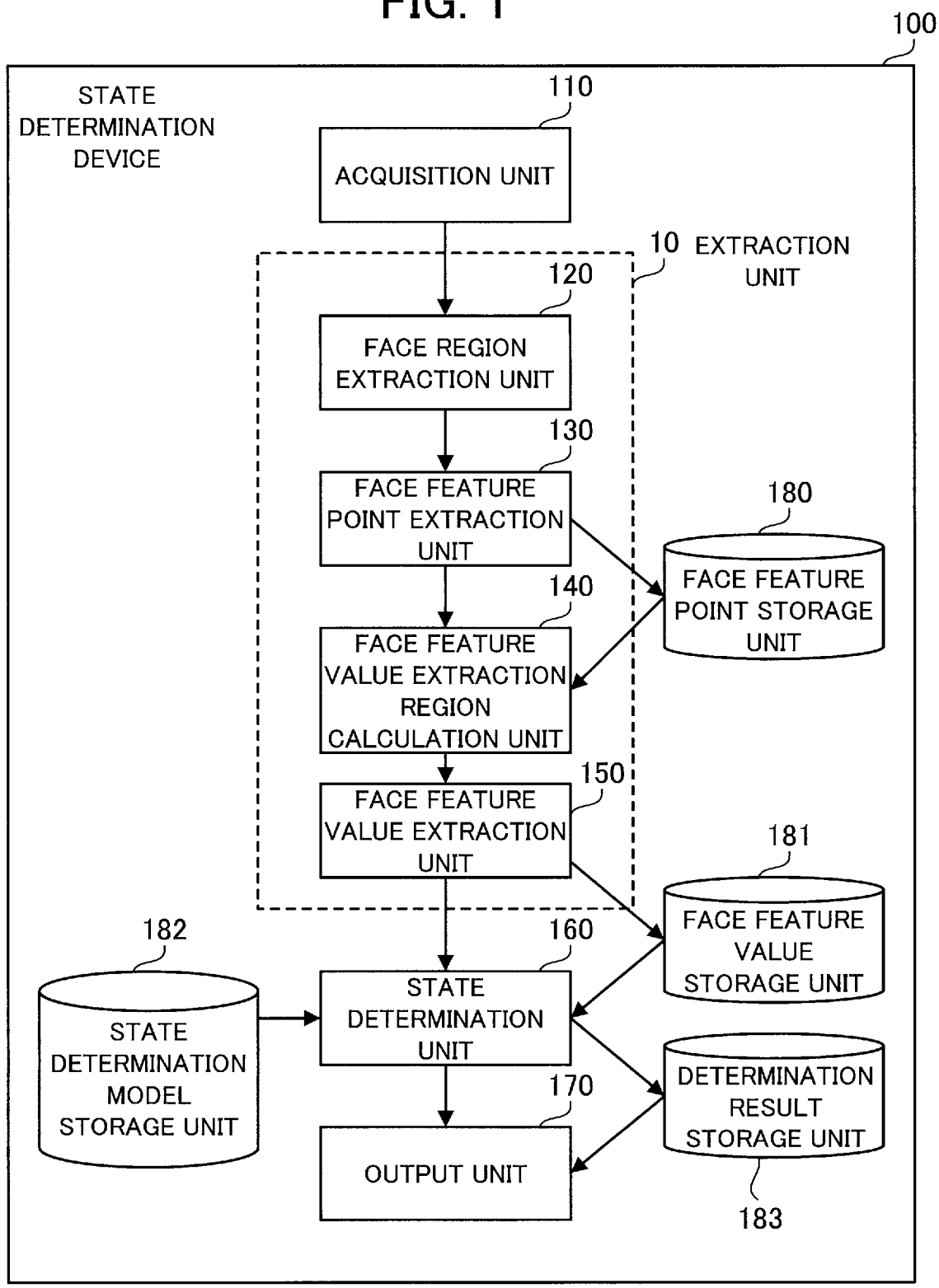
FIG. 1 is a diagram showing a state determination device in a first embodiment.

FIG. 1 is a diagram showing a state determination device in a first embodiment. The state determination device 100 is a device that executes a state determination method.

The state determination device 100 makes a determination of the unawakened state. The unawakened state is, for example, a dozing state, a state of dozing off due to drinking, or the like. The unawakened state includes a state of being in a haze. The state of being in a haze is, for example, a state in which a user is feeling drowsy, a state in which the user is intoxicated from drinking, or the like. Incidentally, there are cases where the user temporarily shifts from the dozing state to an awakened state and thereafter falls into the dozing state again. In such situations where the user falls into the dozing state again in a short time after going out of the dozing state, the user can be considered to be in the dozing state. Therefore, the unawakened state includes cases where the user temporarily shifts from the dozing state to the awakened state and thereafter falls into the dozing state again.

Next, hardware included in the state determination device 100 will be described below.

FIG. 2 is a diagram showing the configuration of the hardware included in the state determination device in the first embodiment. The state determination device 100 includes a processor 101, a volatile storage device 102, a nonvolatile storage device 103, a camera 104 and a display 105.

The processor 101 controls the whole of the state determination device 100. For example, the processor 101 is a Central Processing Unit (CPU), a Field Programmable Gate Array (FPGA) or the like. The processor 101 can also be a multiprocessor. The state determination device 100 may also be implemented by a processing circuitry or implemented by software, firmware or a combination of software and firmware. Incidentally, the processing circuitry may be either a single circuit or a combined circuit.

The volatile storage device 102 is main storage of the state determination device 100. The volatile storage device 102 is a Random Access Memory (RAM), for example. The nonvolatile storage device 103 is auxiliary storage of the state determination device 100. The nonvolatile storage device 103 is a Solid State Drive (SSD), for example.

The camera 104 is a device that captures images of a face. The camera 104 is referred to also as an image capturing device. The display 105 is a device that displays information. The display 105 is referred to also as a display device.

Incidentally, the state determination device 100 in a condition of not including the camera 104 or the display 105 may be regarded as an information processing device.

Returning to FIG. 1, the state determination device 100 will be described below.

The state determination device 100 includes an acquisition unit 110, an extraction unit 10, a state determination unit 160 and an output unit 170. The extraction unit 10 includes a face region extraction unit 120, a face feature point extraction unit 130, a face feature value extraction region calculation unit 140 and a face feature value extraction unit 150.

Further, the state determination device 100 includes a face feature point storage unit 180, a face feature value storage unit 181, a state determination model storage unit 182 and a determination result storage unit 183.

Part or all of the extraction unit 10, the acquisition unit 110, the face region extraction unit 120, the face feature point extraction unit 130, the face feature value extraction region calculation unit 140, the face feature value extraction unit 150, the state determination unit 160 and the output unit 170 may be implemented by the processor 101.

Further, part or all of the extraction unit 10, the acquisition unit 110, the face region extraction unit 120, the face feature point extraction unit 130, the face feature value extraction region calculation unit 140, the face feature value extraction unit 150, the state determination unit 160 and the output unit 170 may be implemented as a module of a program executed by the processor 101. For example, the program executed by the processor 101 is referred to also as a state determination program. The state determination program is stored in a record medium such as the volatile storage device 102 or the nonvolatile storage device 103, for example.

The face feature point storage unit 180, the face feature value storage unit 181, the state determination model storage unit 182 and the determination result storage unit 183 may be implemented as storage areas secured in the volatile storage device 102 or the nonvolatile storage device 103.

The acquisition unit 110 acquires a plurality of frames, successively obtained by capturing images of a user's face, from the camera 104. The plurality of frames may also be represented as motion video. The frame is an image. Further, the plurality of frames may also be represented as a plurality of frames in which the user's face was captured at different times.

The extraction unit 10 extracts a face region from each of the plurality of frames, extracts face feature points from the face region, calculates a face feature value extraction region based on the face feature points, and extracts a face feature value from the face feature value extraction region. Incidentally, the face region represents a region corresponding to the face. The feature point represents a part of the face. The face feature value extraction region is a region where a change occurs in the face region when the user is in the unawakened state. The face feature value is a feature value. Further, the face feature value extraction region may also be represented as a region where a change occurs in the face region when the user is in the unawakened state and where no individual difference occurs as a user's facial movement when the user is in the unawakened state.

Processes executed by the extraction unit 10 will be described in detail below by using the face region extraction unit 120, the face feature point extraction unit 130, the face feature value extraction region calculation unit 140 and the face feature value extraction unit 150.

The face region extraction unit 120 extracts the face region from the motion video. The face region extraction unit 120 may be implemented by use of a discriminator that uses Haar-like features by means of Adaboost learning. A method of extracting the face region is described in Non-patent Reference 1, for example.

The face feature point extraction unit 130 extracts face feature points of an outline, eyebrows, eyes, a nose, a mouth, etc. based on the face region. A method of extracting the face feature points is described in Non-patent Reference 2, for example.

The face feature point extraction unit 130 stores the face feature points in the face feature point storage unit 180. Here, an explanation will be given of the face feature point storage unit 180. The face feature point storage unit 180 stores a face feature point table.

FIG. 3 is a diagram showing an example of the face feature point table in the first embodiment. The face feature point table 180a is stored in the face feature point storage unit 180. The face feature point table 180a includes an item of feature point/face direction. Further, the face feature point table 180a includes an item of coordinates/angle.

For example, coordinates where the face feature point extraction unit 130 extracted a left eye inner end are registered in the face feature point table 180a. Incidentally, the left eye inner end is referred to also as a left eye inner corner.

The face feature point extraction unit 130 calculates the face direction based on the face feature points. The face direction is represented by Yaw, Pitch and Roll. The face feature point extraction unit 130 registers the face direction in the face feature point table 180a.

Returning to FIG. 1, the face feature value extraction region calculation unit 140 will be described below.

The face feature value extraction region calculation unit 140 calculates an extraction region of a face feature value to be used for the determination of the unawakened state.

Here, as an action the user performs when the user is in the unawakened state or an action presaging the user's unawakened state, the user performs an action of resisting sleepiness. The action of resisting sleepiness is the user's action of intentionally closing eyes tightly. The action of resisting sleepiness may also be expressed as strong nictation in which the user intentionally closes eyes tightly. When the user intentionally closes eyes tightly, wrinkles occur on the glabella between the eyebrows. Therefore, the face feature value extraction region calculation unit 140 calculates a glabella region in the face region as the face feature value extraction region.

Further, in cases where the user is in a state like the unawakened state due to drinking, the user licks the user's lips to moisten the dry mouth. Therefore, the face feature value extraction region calculation unit 140 calculates a mouth region in the face region as the face feature value extraction region.

Furthermore, as an action the user performs when the user is in the unawakened state or an action presaging the user's unawakened state, the user yawns. When the user yawns, the mouth opens. Further, when the user yawns, wrinkles occur on the cheeks. Therefore, the face feature value extraction region calculation unit 140 calculates the mouth region and a cheek region in the face region as the face feature value extraction regions.

Here, the calculation of the glabella region and the calculation of the mouth region will be described below as concrete examples.

Figure 4A:
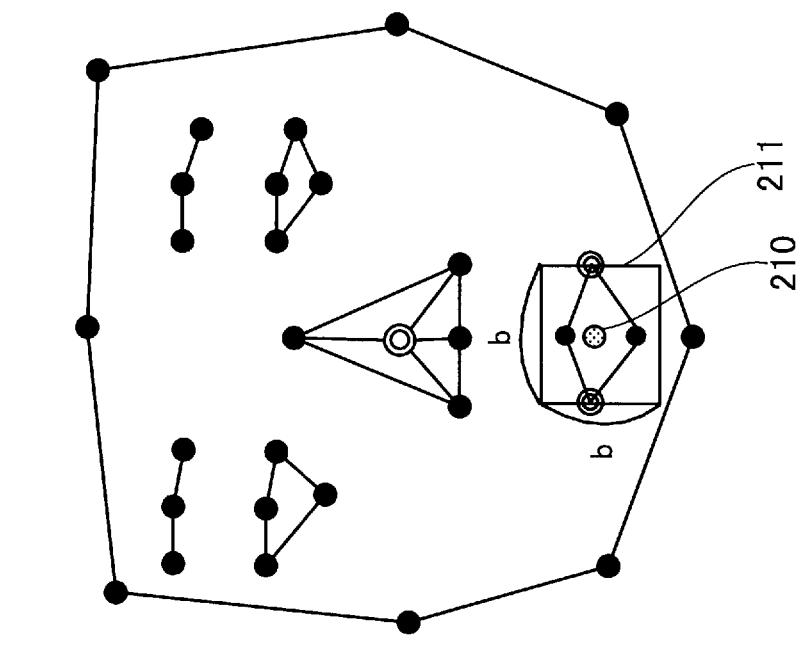
FIGS. 4(A) and 4(B) are diagrams showing examples of calculation of a face feature value extraction region.
Figure 4B:
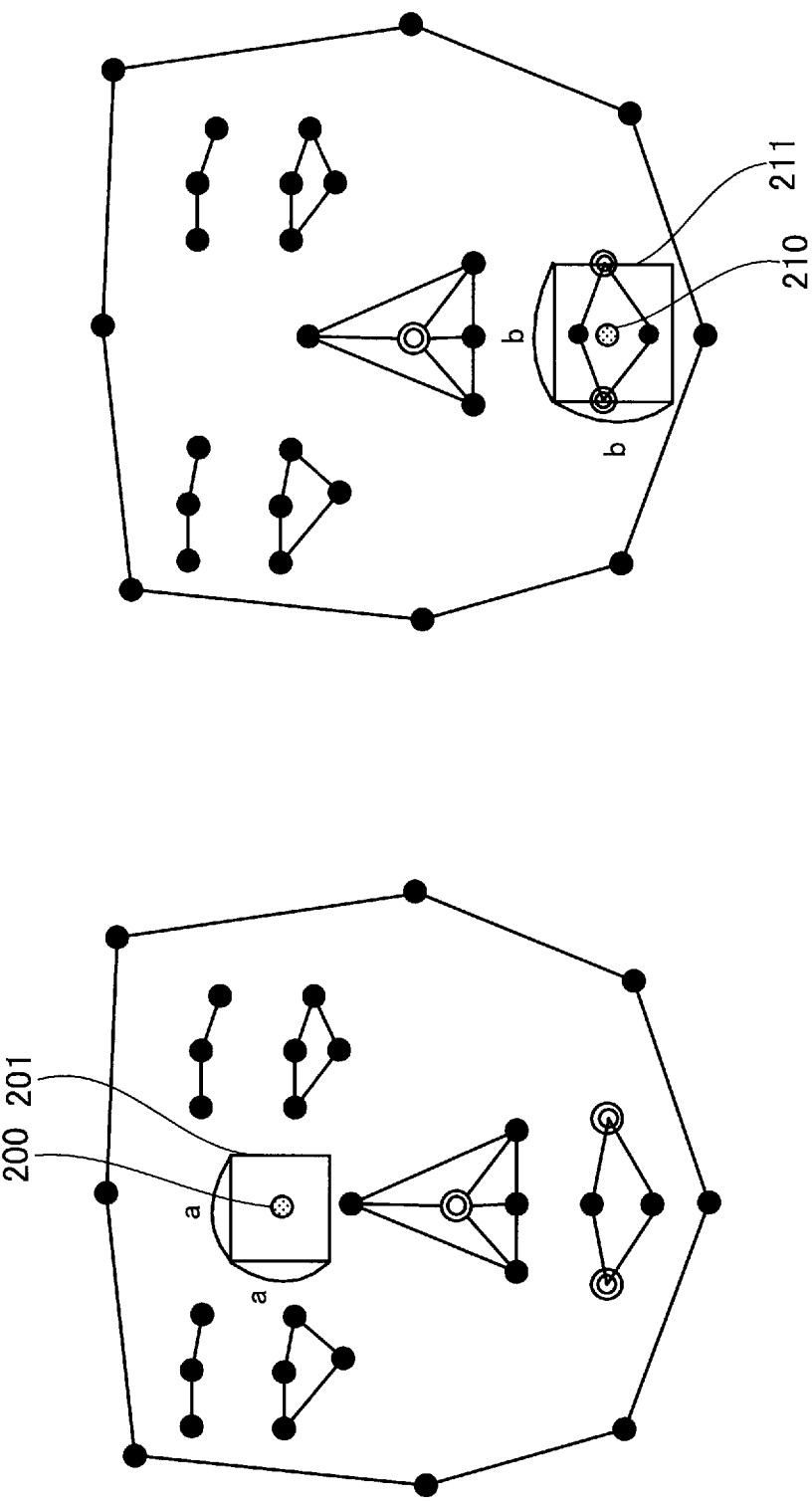

FIGS. 4(A) and 4(B) are diagrams showing examples of the calculation of the face feature value extraction region. FIG. 4(A) shows an example of the calculation of the glabella region. The face feature value extraction region calculation unit 140 identifies a left eye inner corner and a right eye inner corner among the face feature points extracted by the face feature point extraction unit 130. The face feature value extraction region calculation unit 140 calculates a midpoint 200 between the left eye inner corner and the right eye inner corner. The face feature value extraction region calculation unit 140 calculates a rectangular region 201 (i.e., a region of a [pixels]×a [pixels]) centering at the midpoint 200. The rectangular region 201 is the glabella region. The face feature value extraction region calculation unit 140 calculates the glabella region as above.

Further, the face feature value extraction region calculation unit 140 multiplies the length of each side of the rectangular region 201 by k based on a rectangular region corresponding to the face region extracted by the face region extraction unit 120. By this method, the face feature value extraction region calculation unit 140 is capable of calculating a rectangular region of (a×k) [pixels]×(a×k) [pixels].

Incidentally, there are cases where the glabella region is not calculated precisely depending on the face direction. Thus, the face feature value extraction region calculation unit 140 may also calculate the glabella region based on the face direction calculated by the face feature point extraction unit 130 and the midpoint. The calculation will be explained concretely below. It is assumed here that the face is pointed in a left direction, for example. When the face is pointed in the left direction, the center of the region where the glabella wrinkles occur is at a position to the left of the midpoint between the left eye inner corner and the right eye inner corner. Therefore, the face feature value extraction region calculation unit 140 calculates coordinates to which the midpoint has been translated leftward by l [pixels] as central coordinates of the glabella region. The face feature value extraction region calculation unit 140 calculates a rectangular region centering at the central coordinates.

FIG. 4(B) shows an example of the calculation of the mouth region. The face feature value extraction region calculation unit 140 identifies left and right corners of the mouth among the face feature points extracted by the face feature point extraction unit 130. The face feature value extraction region calculation unit 140 calculates a midpoint 210 between the left and right corners of the mouth. The face feature value extraction region calculation unit 140 calculates a rectangular region 211 (i.e., a region of b [pixels]×b [pixels]) centering at the midpoint 210. The rectangular region 211 is the mouth region. The face feature value extraction region calculation unit 140 calculates the mouth region as above.

Further, the face feature value extraction region calculation unit 140 multiplies the length of each side of the rectangular region 211 by k based on the rectangular region corresponding to the face region extracted by the face region extraction unit 120. By this method, the face feature value extraction region calculation unit 140 is capable of calculating a rectangular region of (b×k) [pixels]×(b×k) [pixels].

Furthermore, the face feature value extraction region calculation unit 140 may also calculate the mouth region based on the face feature points and the face direction calculated by the face feature point extraction unit 130. The method of the calculation is as described above.

The face feature value extraction region calculation unit 140 is capable of calculating the cheek region in a similar manner.

Returning to FIG. 1, the face feature value extraction unit 150 will be described below.

The face feature value extraction unit 150 extracts face feature values based on the glabella region, the mouth region and the cheek region. The face feature values are Histograms of Oriented Gradients (HOG) feature values. The HOG feature values are described in Non-patent Reference 3, for example.

The face feature values may also be feature values other than the HOG feature values. For example, the face feature values may be Scaled Invariance Feature Transform (SIFT) feature values, Speeded-Up Robust Features (SURF), Haar-like feature values, or the like.

The face feature value extraction unit 150 stores the face feature values in the face feature value storage unit 181. Here, an explanation will be given of the face feature value storage unit 181. The face feature value storage unit 181 stores a face feature value table.

FIG. 5 is a diagram showing an example of the face feature value table in the first embodiment. The face feature value table 181*a* is stored in the face feature value storage unit 181. The face feature value table 181*a* includes items of a feature value and a value. The face feature value extraction unit 150 registers the face feature values in the face feature value table 181*a*. Specifically, the face feature value extraction unit 150 registers information representing the face feature values in the feature value item of the face feature value table 181*a*. Then, the face feature value extraction unit 150 registers values corresponding to the face feature values in the value item of the face feature value table 181*a*.

Further, HOG feature values respectively corresponding to n frames (n: integer larger than or equal to 2) acquired by the acquisition unit 110 in predetermined time are registered in the face feature value table 181*a*. Incidentally, the predetermined time is five minutes, for example.

Returning to FIG. 1, the state determination unit 160 will be described below.

The state determination unit 160 determines whether the user is in the unawakened state or not based on the face feature values in each of the plurality of frames and previously generated determination information. The state determination unit 160 may also be described to determine whether the user is in the unawakened state or not based on the face feature values corresponding to each of the plurality of frames and previously stored determination information.

The state determination unit 160 will be described in detail below.

The state determination unit 160 makes the determination of the unawakened state based on the HOG feature values. Specifically, the state determination unit 160 makes the determination of the unawakened state based on the numbers of times of the aforementioned three actions performed by the user in predetermined time. Incidentally, the three actions are the user's action of wrinkling the user's glabella, the user's action of licking the lips to moisten the dry mouth, and the user's action of yawning. The predetermined time is five minutes, for example.

Here, information for making the determination of the unawakened state has been stored in the state determination model storage unit 182. Incidentally, this information has previously been stored in the state determination model storage unit 182 before the state determination device 100 executes the determination of the unawakened state.

This information is referred to as a state determination model table. The state determination model table will be described below.

FIG. 6 is a diagram showing an example of the state determination model table in the first embodiment. The state determination model table 182*a* is stored in the state determination model storage unit 182. The state determination model table 182*a* includes items of an unawakenedness level, the number of times of wrinkling the glabella in five minutes, the number of times of licking the lips in five minutes, and the number of times of yawning in five minutes.

The state determination model table 182*a* is referred to also as the determination information. Further, the state determination model table 182*a* includes information for determining an unawakenedness level according to the number of times the user wrinkled the glabella. The state determination model table 182*a* includes information for determining an unawakenedness level according to the number of times the user licked the lips. The state determination model table 182*a* includes information for determining an unawakenedness level according to the number of times the user yawned.

Here, a description will be given of a method by which the state determination unit 160 determines that the glabella was wrinkled. The state determination unit 160 calculates cosine similarity Sn by using the following expression (1):

$$S_n = \cos(\overrightarrow{H_n}, \overrightarrow{H_m}) = \frac{\overrightarrow{H_n} \cdot \overrightarrow{H_m}}{|\overrightarrow{H_n}||\overrightarrow{H_m}|} = \frac{\overrightarrow{H_n}}{|\overrightarrow{H_n}|} \cdot \frac{\overrightarrow{H_m}}{|\overrightarrow{H_m}|} = \frac{\sum_{i=1}^{n} H_{n_i} H_{m_i}}{\sqrt{\sum_{i=1}^{n} H_{n_i}^2} \cdot \sqrt{\sum_{i=1}^{n} H_{m_i}^2}} \quad (1)$$

A mean value Hm is a mean value of HOG feature values extracted by the face feature value extraction unit 150 from a plurality of frames in a very awake state (i.e., normal state). Incidentally, the mean value Hm is previously calculated before the state determination device 100 executes the determination of the unawakened state. The mean value Hm has been stored in the face feature value storage unit 181, for example.

HOG feature values Hn are HOG feature values corresponding to n frames acquired by the acquisition unit 110 in the predetermined time.

Here, a diagram showing an example of the relationship between the cosine similarity Sn and the time will be explained.

Figure 7:
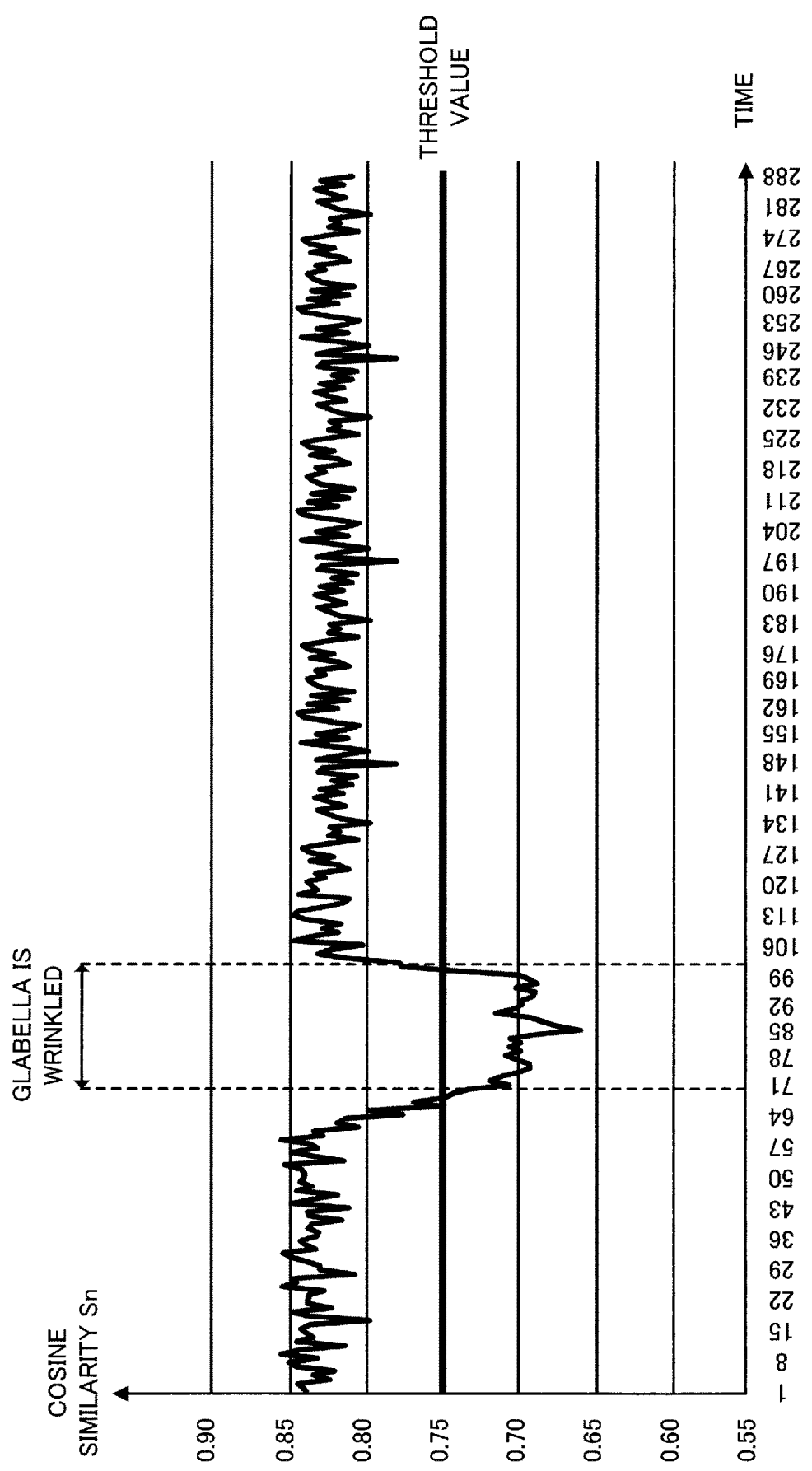
FIG. 7 is a diagram for explaining a method of calculating the number of times of wrinkling a glabella between eyebrows in the first embodiment.

FIG. 7 is a diagram for explaining a method of calculating the number of times of wrinkling the glabella in the first embodiment. The vertical axis of the graph in FIG. 7 represents the cosine similarity Sn. The horizontal axis of the graph in FIG. 7 represents the time. When the glabella is wrinkled, edges of the wrinkles appear intensely. When the edges of the wrinkles appear intensely, the cosine similarity Sn takes on a low value.

When the cosine similarity Sn is lower than a predetermined threshold value S, the state determination unit 160 determines that the glabella was wrinkled. When the state determination unit 160 determines that the glabella was wrinkled, the state determination unit 160 increments the number of times of wrinkling the glabella.

The method of determining that the glabella was wrinkled and a method of determining that the user licked the lips are similar methods. Further, the method of determining that the glabella was wrinkled and a method of determining that the user yawned are similar methods. Therefore, the explanation is omitted for the method of determining that the user licked the lips and the method of determining that the user yawned.

As above, the state determination unit 160 calculates the number of times the user wrinkled the glabella based on the face feature value extracted from the glabella region in each of the plurality of frames. The state determination unit 160 calculates the number of times the user licked the lips based on the face feature value extracted from the mouth region in each of the plurality of frames. The state determination unit 160 calculates the number of times the user yawned based on the face feature values extracted from the mouth region and the cheek region in each of the plurality of frames.

The state determination unit 160 determines the unawakenedness level based on the number of times of wrinkling the glabella and the state determination model table 182a. The state determination unit 160 determines the unawakenedness level based on the number of times of licking the lips and the state determination model table 182a. The state determination unit 160 determines the unawakenedness level based on the number of times of yawning and the state determination model table 182a.

Figure 8:
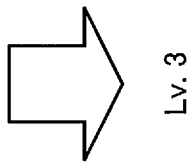
FIG. 8 is a diagram showing a concrete example of an unawakenedness level in the first embodiment.

FIG. 8 is a diagram showing a concrete example of the unawakenedness level in the first embodiment. FIG. 8 indicates that the unawakenedness level determined based on the number of times of wrinkling the glabella is level 2. FIG. 8 indicates that the unawakenedness level determined based on the number of times of licking the lips is level 4. FIG. 8 indicates that the unawakenedness level determined based on the number of times of yawning is level 3.

The state determination unit 160 calculates the mean value of the three unawakenedness levels. For example, the state determination unit 160 calculates the level 3 ($=(2+4+3)/3$) as the mean value. The state determination unit 160 may also round off the mean value to the nearest integer.

If the mean value is higher than or equal to a predetermined threshold value, the state determination unit 160 determines that the user is in the unawakened state. The threshold value is 3, for example. Incidentally, this threshold value is referred to also as a threshold level. As above, the state determination unit 160 determines that the user is in the unawakened state if the mean value is higher than or equal to the level 3. Incidentally, which level should be determined as the unawakened state can be changed depending on the method of evaluation.

The state determination unit 160 stores a determination result in the determination result storage unit 183. The determination result is the mean value. Here, an explanation will be given of the determination result storage unit 183. The determination result storage unit 183 stores a determination result table.

Figure 9:
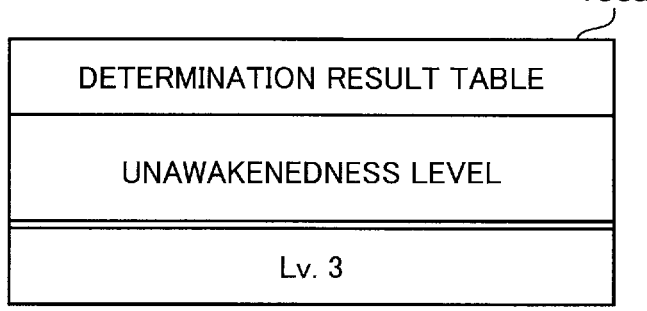
FIG. 9 is a diagram showing an example of a determination result table in the first embodiment.

FIG. 9 is a diagram showing an example of the determination result table in the first embodiment. The determination result table 183a is stored in the determination result storage unit 183. The determination result table 183a includes an item of the unawakenedness level. The state determination unit 160 registers the calculated mean value in the in the determination result table 183a.

The state determination unit 160 may also make the determination of the unawakened state based on information obtained by executing machine learning by using Random Forest, Support Vector Machine (SVM), Adaboost, Convolutional Neural Network (CNN) or the like and the face feature values. Incidentally, this information is referred to also as determination information. Namely, the determination information is information obtained by means of machine learning and information for determining whether the user is in the unawakened state or not.

Returning to FIG. 1, the output unit 170 will be described below. The output unit 170 outputs the determination result. The output unit 170 will be described in detail below.

The output unit 170 outputs the unawakenedness level registered in the determination result table 183a. For example, the output unit 170 outputs the unawakenedness level to the display 105. Alternatively, the output unit 170 may output the unawakenedness level as audio. Incidentally, the unawakenedness level registered in the determination result table 183a is referred to also as information representing the mean value.

The output unit 170 may also output information indicating that the user is in the unawakened state when the unawakenedness level registered in the determination result table 183a is higher than or equal to level 3. The output unit 170 may also output information indicating that the user is not in the unawakened state when the unawakenedness level registered in the determination result table 183a is lower than or equal to level 2.

Next, processes executed by the state determination device 100 will be described below by using flowcharts.

Figure 10:
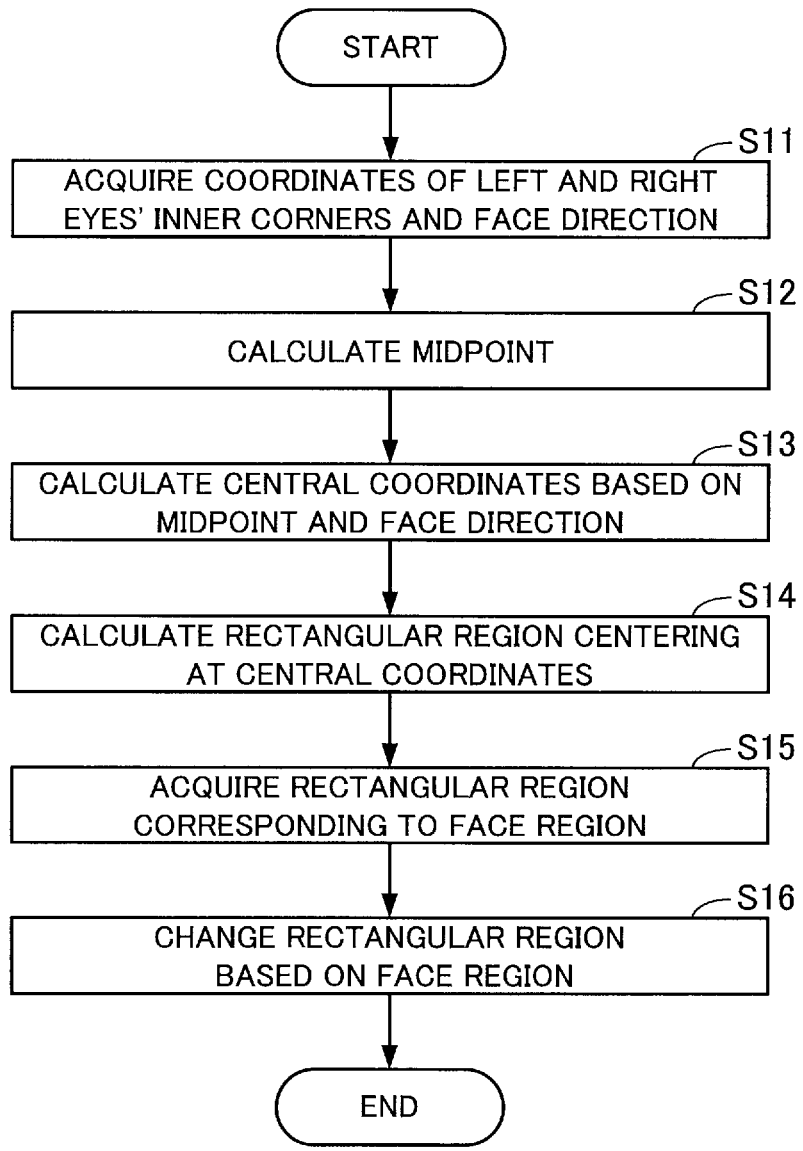
FIG. 10 is a flowchart showing a face feature value extraction region calculation process in the first embodiment.

FIG. 10 is a flowchart showing a face feature value extraction region calculation process in the first embodiment. Incidentally, a glabella region calculation process will be described below with reference to FIG. 10. FIG. 10 shows an example of a process executed by the face feature value extraction region calculation unit 140.

(Step S11) The face feature value extraction region calculation unit 140 acquires the coordinates of the left eye inner corner and the right eye inner corner and the face direction from the face feature point storage unit 180.

(Step S12) The face feature value extraction region calculation unit 140 calculates the midpoint between the left eye inner corner and the right eye inner corner.

(Step S13) The face feature value extraction region calculation unit 140 calculates the central coordinates based on the midpoint and the face direction. Specifically, the face feature value extraction region calculation unit 140 calculates the central coordinates as coordinates to which the midpoint has been translated.

(Step S14) The face feature value extraction region calculation unit 140 calculates the rectangular region centering at the central coordinates.

(Step S15) The face feature value extraction region calculation unit 140 acquires the rectangular region corresponding to the face region extracted by the face region extraction unit 120.

(Step S16) The face feature value extraction region calculation unit 140 changes the size of the rectangular region calculated in the step S14 based on the rectangular region corresponding to the face region. For example, the face feature value extraction region calculation unit 140 multiplies the length of each side of the rectangular region by k based on the rectangular region corresponding to the face region. By this method, the glabella region according to the size of the face is calculated.

The face feature value extraction region calculation unit 140 is capable of calculating the mouth region and the cheek region by processes similar to the above-described process.

Figure 11:
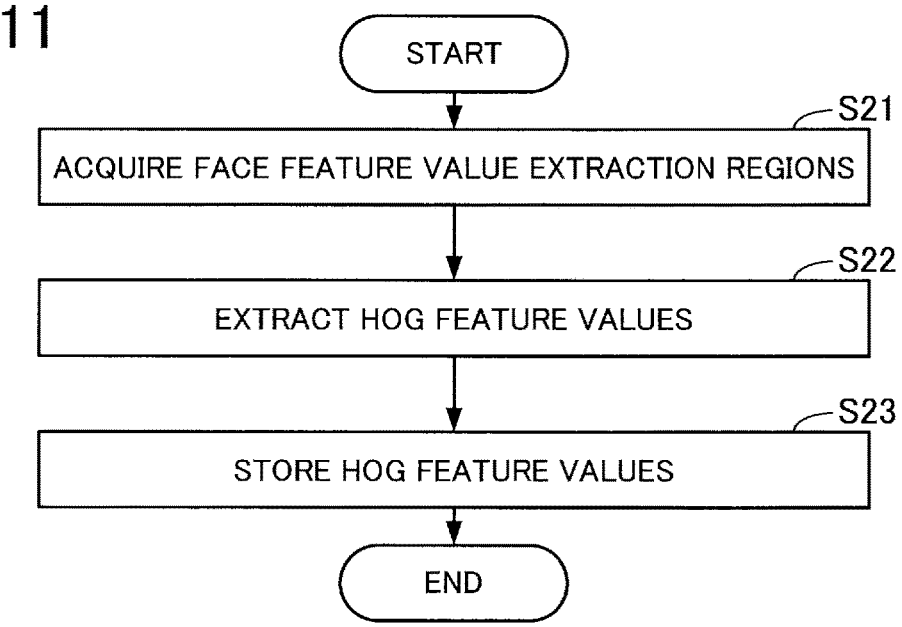
FIG. 11 is a flowchart showing a face feature value extraction process in the first embodiment.

FIG. 11 is a flowchart showing a face feature value extraction process in the first embodiment.

(Step S21) The face feature value extraction unit 150 acquires the three face feature value extraction regions calculated by the face feature value extraction region calculation unit 140. Specifically, the three face feature value extraction regions are the glabella region, the mouth region and the cheek region.

(Step S22) The face feature value extraction unit 150 extracts a HOG feature value based on the glabella region. Further, the face feature value extraction unit 150 extracts a HOG feature value based on the mouth region. Furthermore, the face feature value extraction unit 150 extracts a HOG feature value based on the cheek region.

(Step S23) The face feature value extraction unit 150 stores the HOG feature value extracted based on the glabella region in the face feature value storage unit 181. Further, the face feature value extraction unit 150 stores the HOG feature value extracted based on the mouth region in the face feature value storage unit 181. Furthermore, the face feature value extraction unit 150 stores the HOG feature value extracted based on the cheek region in the face feature value storage unit 181.

By this process, the HOG feature values respectively extracted based on the three face feature value extraction regions are registered in the face feature value table 181a.

Figure 12:
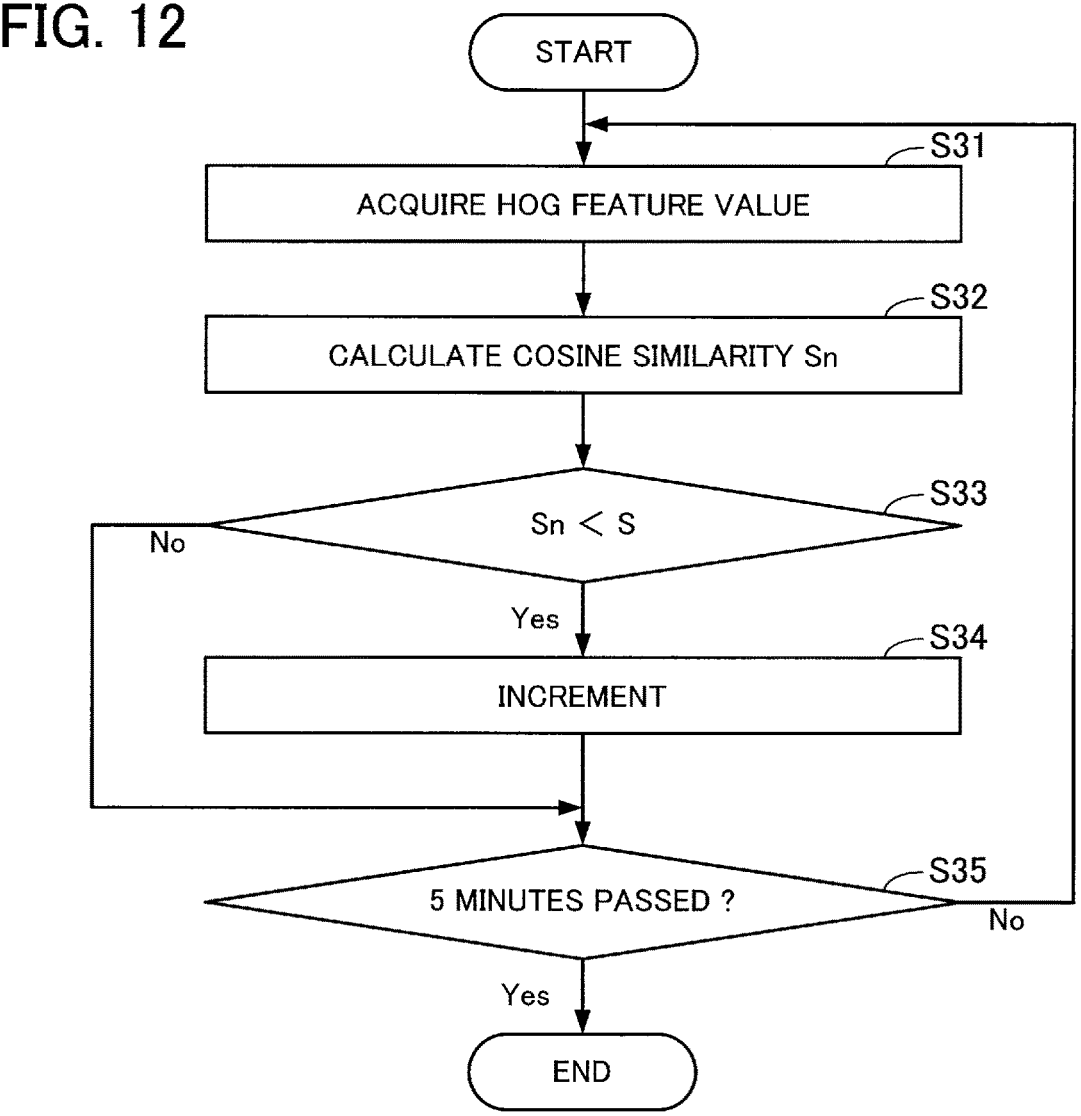
FIG. 12 is a flowchart showing a count process in the first embodiment.

FIG. 12 is a flowchart showing a count process in the first embodiment. A case of counting the number of times of wrinkling the glabella will be explained below with reference to FIG. 12.

(Step S31) The state determination unit 160 acquires a HOG feature value extracted based on the glabella region extracted from one frame (referred to as a first frame, for example) from the face feature value storage unit 181.

(Step S32) The state determination unit 160 calculates the cosine similarity Sn by using the expression (1).

(Step S33) The state determination unit 160 judges whether or not the cosine similarity Sn calculated in the step S32 is lower than the threshold value S.

The case where the cosine similarity Sn calculated in the step S32 is lower than the threshold value S is a case where the edges of the wrinkles on the glabella appear intensely, for example. Put another way, the case where the cosine similarity Sn calculated in the step S32 is lower than the threshold value S is a case where the user is wrinkling the glabella.

When the judgment condition is satisfied, the state determination unit 160 advances the process to step S34. When the judgment condition is not satisfied, the state determination unit 160 advances the process to step S35.

(Step S34) The state determination unit 160 increments the number of times of wrinkling the glabella.

(Step S35) The state determination unit 160 judges whether or not five minutes have passed since the start of the count process. If five minutes have passed, the state determination unit 160 ends the process. If five minutes have not passed, the state determination unit 160 advances the process to the step S31. In this step S31, for example, the state determination unit 160 acquires a HOG feature value extracted based on the glabella region extracted from a second frame acquired by the acquisition unit 110 next to the first frame, from the face feature value storage unit 181.

As above, the state determination unit 160 acquires the HOG feature values respectively extracted based on the glabella region in the n frames acquired by the acquisition unit 110 in five minutes. The state determination unit 160 determines whether the glabella was wrinkled or not based on each of the HOG feature values. By this process, the state determination unit 160 is capable of obtaining the number of times the user wrinkled the glabella in five minutes.

The number of times of licking the lips is obtained by a method similar to the count process shown in FIG. 11. For example, the glabella region mentioned in the step S31 is changed to the mouth region. By this process, the state determination unit 160 is capable of obtaining the number of times the user licked the lips in five minutes.

Further, the number of times of yawning is obtained by a method similar to the count process shown in FIG. 11. For example, the glabella region mentioned in the step S31 is changed to the mouth region and the cheek region. In the step S33, for example, the state determination unit 160 advances the process to the step S34 when the cosine similarity Sn calculated based on the HOG feature value corresponding to the mouth region and the cosine similarity Sn calculated based on the HOG feature value corresponding to the cheek region are lower than a predetermined threshold value. By this process, the state determination unit 160 is capable of obtaining the number of times the user yawned in five minutes.

Incidentally, the aforementioned five minutes is an arbitrarily set time. Thus, the time mentioned as five minutes can also be a time different from five minutes.

Figure 13:
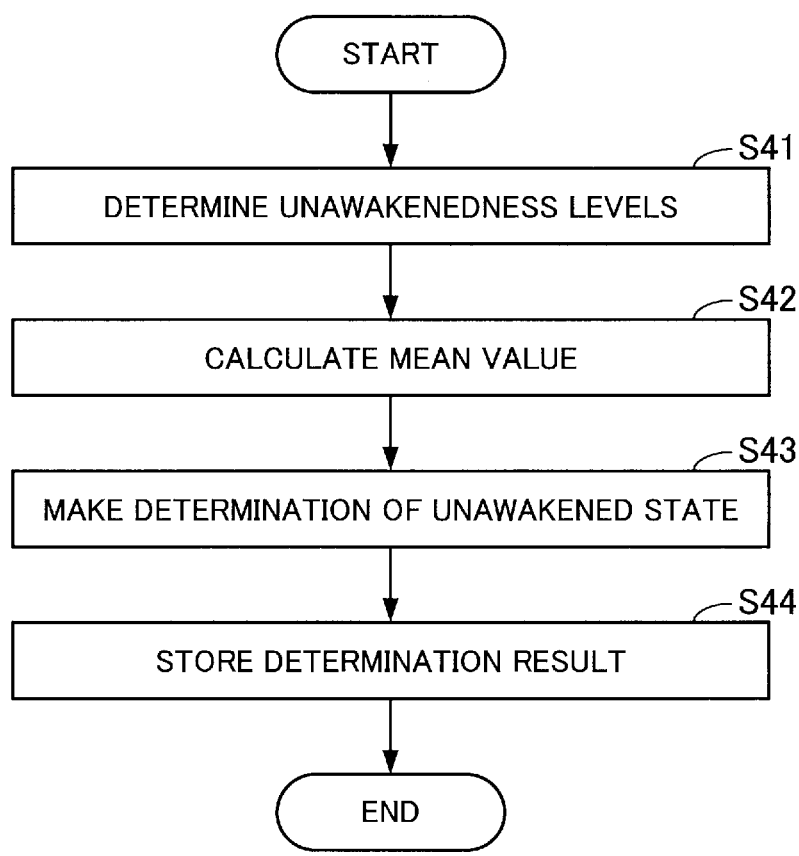
FIG. 13 is a flowchart showing an unawakened state determination process in the first embodiment.

FIG. 13 is a flowchart showing an unawakened state determination process in the first embodiment.

(Step S41) The state determination unit 160 determines the unawakenedness level based on the state determination model table 182a and the number of times of wrinkling the glabella. The state determination unit 160 determines the unawakenedness level based on the state determination model table 182a and the number of times of licking the lips. The state determination unit 160 determines the unawakenedness level based on the state determination model table 182a and the number of times of yawning.

(Step S42) The state determination unit 160 calculates the mean value based on the three unawakenedness levels. The state determination unit 160 may also round off the mean value to the nearest integer.

(Step S43) The state determination unit 160 makes the determination of the unawakened state based on the mean value. For example, the state determination unit 160 determines that the user is in the unawakened state if the mean value is higher than or equal to the level 3.

(Step S44) The state determination unit 160 stores the determination result in the determination result storage unit 183.

According to the first embodiment, the state determination device 100 determines whether the user is in the unawakened state or not based on the user's action of wrinkling the glabella, the user's action of licking the lips, and the user's action of yawning. There is little individual difference or no individual difference in regard to the three actions in the unawakened state. Since the state determination device 100 makes the determination of the unawakened state based on the user's actions regarding which there is little individual difference or no individual difference, the determination of the unawakened state can be made with high accuracy.

Further, the state determination unit 160 may determine the unawakenedness level based on the number of times the user wrinkled the glabella and the state determination model table 182a and determine that the user is in the unawakened state if the determined unawakenedness level is higher than or equal to a predetermined threshold level. The threshold level is level 3, for example. The output unit 170 may output the determined unawakenedness level.

Furthermore, the state determination unit 160 may determine the unawakenedness level based on the number of times the user licked the lips and the state determination model table 182a and determine that the user is in the unawakened state if the determined unawakenedness level is higher than or equal to a predetermined threshold level. The threshold level is level 3, for example. The output unit 170 may output the determined unawakenedness level.

Moreover, the state determination unit 160 may determine the unawakenedness level based on the number of times the user yawned and the state determination model table 182a and determine that the user is in the unawakened state if the determined unawakenedness level is higher than or equal to a predetermined threshold level. The threshold level is level 3, for example. The output unit 170 may output the determined unawakenedness level.

A case where the state determination unit 160 determines whether the user is in the unawakened state or not based on the mean value of the three unawakenedness levels has been described above. The state determination unit 160 may also determine whether the user is in the unawakened state or not based on a mean value of two unawakenedness levels. For example, the state determination unit 160 determines whether the user is in the unawakened state or not based on the mean value of the unawakenedness level based on the number of times the user wrinkled the glabella and the unawakenedness level based on the number of times the user licked the lips.
For example, the state determination unit 160 determines whether the user is in the unawakened state or not based on the mean value of the unawakenedness level based on the number of times the user wrinkled the glabella and the unawakenedness level based on the number of times the user yawned. For example, the state determination unit 160 determines whether the user is in the unawakened state or not based on the mean value of the unawakenedness level based on the number of times the user licked the lips and the unawakenedness level based on the number of times the user yawned.

Second Embodiment

Next, a second embodiment will be described below. The following description of the second embodiment will be given mainly of features different from those in the first embodiment, and the description is omitted for features in common with the first embodiment. FIGS. 1 to 13 are referred to in the second embodiment.

Figure 14:
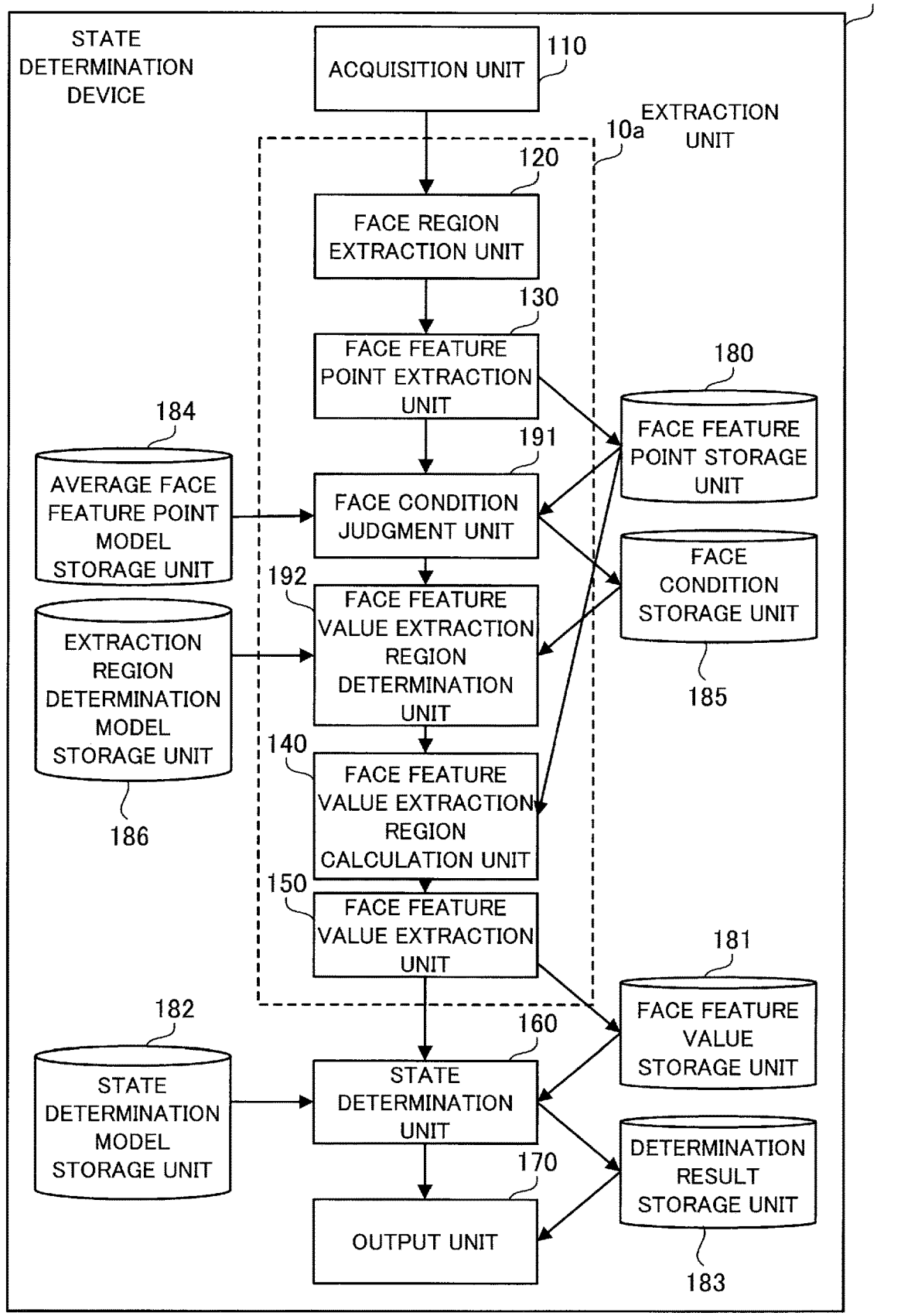
FIG. 14 is a functional block diagram showing a configuration of a state determination device in a second embodiment.

FIG. 14 is a functional block diagram showing the configuration of a state determination device in the second embodiment. The state determination device 100a includes an extraction unit 10a. The extraction unit 10a includes a face condition judgment unit 191 and a face feature value extraction region determination unit 192.

Further, the state determination device 100a includes an average face feature point model storage unit 184, a face condition storage unit 185 and an extraction region determination model storage unit 186.

Part or all of the extraction unit 10a, the face condition judgment unit 191 and the face feature value extraction region determination unit 192 may be implemented by the processor 101. Further, part or all of the extraction unit 10a, the face condition judgment unit 191 and the face feature value extraction region determination unit 192 may be implemented as a module of a program executed by the processor 101. For example, the program executed by the processor 101 is referred to also as a state determination program.

The average face feature point model storage unit 184, the face condition storage unit 185 and the extraction region determination model storage unit 186 may be implemented as storage areas secured in the volatile storage device 102 or the nonvolatile storage device 103.

Components in FIG. 14 identical with those shown in FIG. 1 are assigned the same reference characters as in FIG. 1.

The face condition judgment unit 191 judges whether the user is wearing an attached object or not based on a plurality of frames. For example, when no eye feature point has been extracted as a face feature point, the face condition judgment unit 191 judges that the user is wearing sunglasses. For example, when no mouth feature point has been extracted as a face feature point, the face condition judgment unit 191 judges that the user is wearing a mask.

The face condition judgment unit 191 may also make the judgment on whether the user is wearing an attached object or not as described below. The average face feature point model storage unit 184 will be explained first. The average face feature point model storage unit 184 stores an average face feature point model table.

FIG. 15 is a diagram showing an example of the average face feature point model table in the second embodiment. The average face feature point model table 184a is stored in the average face feature point model storage unit 184. The average face feature point model table 184a has been stored in the average face feature point model storage unit 184, before the state determination device 100a executes the determination of the unawakened state. The average face feature point model table 184a is referred to also as average face feature point model information.

The average face feature point model table 184a includes items of a feature point and average coordinates. The average face feature point model table 184a indicates positions of parts of an average face. For example, a fact that the average position of the left eyebrow outer end on faces of a large number of people is (100, 100) has been registered in the average face feature point model table 184a.

The face condition judgment unit 191 judges whether the user is wearing an attached object or not by using the average face feature point model table 184a and the face feature points. For example, when the distance between the position of a left eye feature point and the position of the average coordinates of the left eye (i.e., the left eye outer end and the left eye inner end) registered in the average face feature point model table 184a is greater than or equal to a threshold value, the face condition judgment unit 191 judges that the reliability regarding the position of the left eye feature point is low. Then, the face condition judgment unit 191 judges that the user is wearing sunglasses. Similarly, when the distance between the position of a mouth feature point and the average coordinates of the mouth registered in the average face feature point model table 184a is greater than or equal to a threshold value, the face condition judgment unit 191 judges that the user is wearing a mask.

Here, when comparing information registered in the average face feature point model table 184a with a face feature point, the face condition judgment unit 191 uses the Euclidean distance or the Mahalanobis distance. Incidentally, when using the Euclidean distance or the Mahalanobis distance, for example, the face condition judgment unit 191 equalizes the distance between the left eye outer end and the right eye outer end extracted by the face feature point extraction unit 130 and the distance between the left eye outer end and the right eye outer end registered in the average face feature point model table 184a with each other. As above, the face condition judgment unit 191 uses the distance between the left eye outer end and the right eye outer end. The face condition judgment unit 191 may also use a distance other than the distance between the left eye outer end and the right eye outer end. For example, the face condition judgment unit 191 uses the distance between the left eyebrow outer end and the right eyebrow outer end.

Further, the face condition judgment unit 191 judges whether or not a shadow is included in any frame among the n frames. Furthermore, the face condition judgment unit 191 judges whether or not a color skip exists in any frame among the plurality of frames. The color skip means blown out highlights, for example. The blown out highlights mean appearance of a white part in the frame. For example, when light is applied from the left by an illuminator, the color skip occurs to a left face part in the frame.

When a shadow/color skip region is included in a frame, the face condition judgment unit 191 performs control so as not to set the shadow/color skip region as the feature value extraction region. Accordingly, the face feature value extraction region calculation unit 140 is capable of calculating an appropriate region as the face feature value extraction region.

Further, when the user is wearing no attached object and no shadow/color skip region is included in the frame, the face condition judgment unit 191 judges that the condition is a normal condition.

The face condition judgment unit 191 stores the judgment result in the face condition storage unit 185. Here, an explanation will be given of the face condition storage unit 185. The face condition storage unit 185 stores a face condition table.

FIGS. 16(A) to 16(C) are diagrams showing examples of the face condition table. The face condition table 185a includes an item of a face condition.

FIG. 16(A) shows a state in which the face condition judgment unit 191 has registered "NORMAL CONDITION" in the face condition table 185a. FIG. 16(B) shows a state in which the face condition judgment unit 191 has registered "WEARING MASK" in the face condition table 185a. FIG. 16(C) shows a state in which the face condition judgment unit 191 has registered "LIGHT APPLIED FROM LEFT" in the face condition table 185a.

When the face condition judgment unit 191 judges that a left half of the face does not exist in the frame based on the face direction, the face condition judgment unit 191 may register "face facing sideways" in the face condition table 185a.

Next, an explanation will be given of the extraction region determination model storage unit 186. The extraction region determination model storage unit 186 stores an extraction region determination model table.

FIG. 17 is a diagram showing an example of the extraction region determination model table in the second embodiment. The extraction region determination model table 186a is stored in the extraction region determination model storage unit 186. The extraction region determination model table 186a has been stored in the extraction region determination model storage unit 186 before the state determination device 100a executes the determination of the unawakened state. The extraction region determination model table 186a includes items of a face condition and a face feature value extraction region. The extraction region determination model table 186a is referred to also as extraction region determination model information. The extraction region determination model table 186a is information indicating which region in the face region should be determined as the face feature value extraction region depending on the position where the attached object has been worn. Further, the extraction region determination model table 186a is information indicating which region in the face region should be determined as the face feature value extraction region depending on the position where a shadow or a color skip exists.

When the user is judged to be wearing an attached object, the face feature value extraction region determination unit 192 determines the face feature value extraction region based on the extraction region determination model table 186a. Specifically, the face feature value extraction region determination unit 192 determines the face feature value extraction region based on the extraction region determination model table 186a and the face condition judged by the face condition judgment unit 191.

Further, when it is judged that a shadow or a color skip exists in any frame among the plurality of frames, the face feature value extraction region determination unit 192 determines the face feature value extraction region based on the extraction region determination model table 186a.

For example, when the face condition judgment unit 191 judges that the user is wearing a mask, the face feature value extraction region determination unit 192 determines the glabella region as the face feature value extraction region. Here, in the case where the user is wearing a mask, it is difficult for the face feature value extraction region calculation unit 140 to calculate the mouth region or the cheek region. Therefore, the face feature value extraction region determination unit 192 performs control so as not to determine the mouth region or the cheek region as the face feature value extraction region. Then, the face feature value extraction region determination unit 192 determines the glabella region as the face feature value extraction region.

The face feature value extraction region calculation unit 140 calculates the face feature value extraction region determined by the face feature value extraction region determination unit 192 based on the face feature points extracted by the face feature point extraction unit 130.

Next, processes executed by the state determination device 100a will be described below by using flowcharts.

Figure 18:
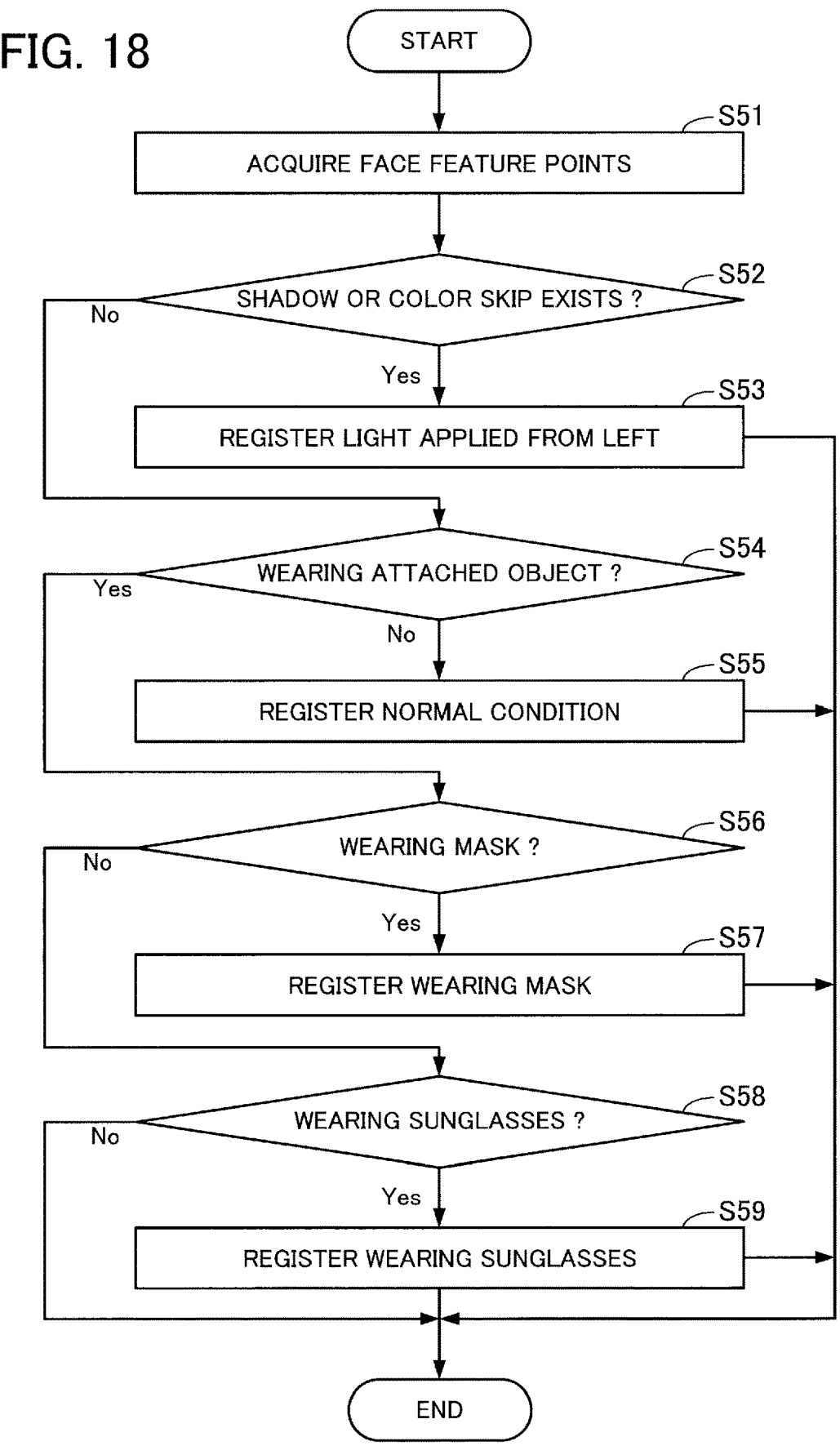
FIG. 18 is a flowchart showing a face condition judgment process in the second embodiment.

FIG. 18 is a flowchart showing a face condition judgment process in the second embodiment. FIG. 18 shows an example of a process executed by the face condition judgment unit 191.

(Step S51) The face condition judgment unit 191 acquires the face feature points from the face feature point storage unit 180.

(Step S52) The face condition judgment unit 191 judges whether or not a shadow or a color skip exists in the frame.

For example, when the color of a certain region of the face in the frame is black, the face condition judgment unit 191 judges that a shadow exists in the frame. For example, when the color of a certain region of the face in the frame is white or no face feature point has been acquired from a certain region in the frame, the face condition judgment unit 191 judges that a color skip exists in the frame. Incidentally, it is assumed in FIG. 18 that the shadow or the color skip occurs due to the application of light from the left by an illuminator Further, when position information indicating the installation position of an illuminator is acquired, the face condition judgment unit 191 may make the judgment on whether or not a shadow or a color skip exists in the frame based on the position information.

When a shadow or a color skip exists in the frame, the face condition judgment unit 191 advances the process to step S53. When no shadow or color skip exists in the frame, the face condition judgment unit 191 advances the process to step S54.

(Step S53) The face condition judgment unit 191 registers "LIGHT APPLIED FROM LEFT" in the face condition table 185a. Then, the face condition judgment unit 191 ends the process.

(Step S54) The face condition judgment unit 191 judges whether or not the user is wearing an attached object. For example, the face condition judgment unit 191 judges that the user is wearing an attached object when no eye feature point has been extracted as a face feature point.

When the user is wearing an attached object, the face condition judgment unit 191 advances the process to step S56. When the user is wearing no attached object, the face condition judgment unit 191 advances the process to step S55.

(Step S55) The face condition judgment unit 191 registers "NORMAL CONDITION" in the face condition table 185a. Then, the face condition judgment unit 191 ends the process.

(Step S56) The face condition judgment unit 191 judges whether or not the user is wearing a mask. For example, the face condition judgment unit 191 judges that the user is wearing a mask when no mouth feature point has been extracted as a face feature point.

When the user is wearing a mask, the face condition judgment unit 191 advances the process to step S57. When the user is not wearing a mask, the face condition judgment unit 191 advances the process to step S58.

(Step S57) The face condition judgment unit 191 registers "WEARING MASK" in the face condition table 185a. Then, the face condition judgment unit 191 ends the process.

(Step S58) The face condition judgment unit 191 judges whether or not the user is wearing sunglasses. For example, the face condition judgment unit 191 judges that the user is wearing sunglasses when no eye feature point has been extracted as a face feature point.

When the user is wearing sunglasses, the face condition judgment unit 191 advances the process to step S59. When the user is not wearing sunglasses, the face condition judgment unit 191 ends the process.

(Step S59) The face condition judgment unit 191 registers "WEARING SUNGLASSES" in the face condition table 185a. Then, the face condition judgment unit 191 ends the process.

Figure 19:
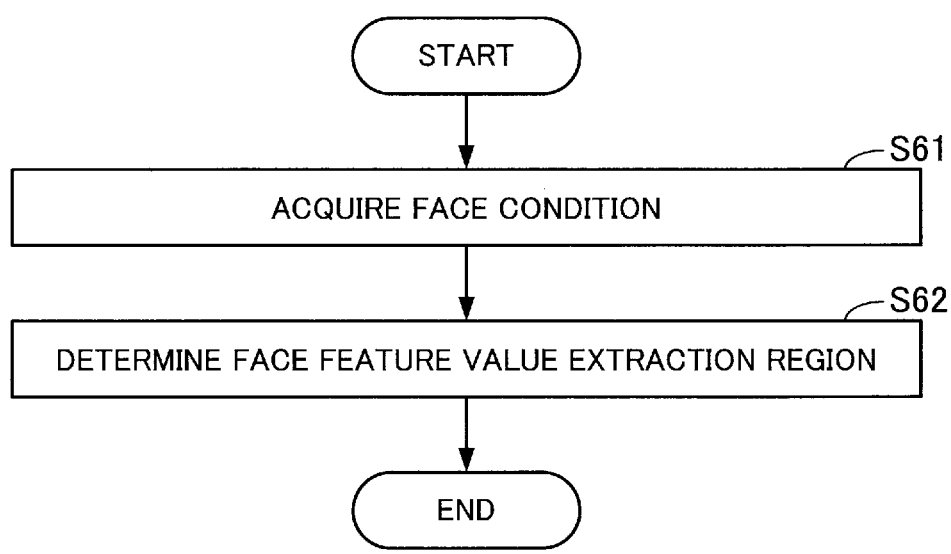
FIG. 19 is a flowchart showing a face feature value extraction region determination process in the second embodiment.

FIG. 19 is a flowchart showing a face feature value extraction region determination process in the second embodiment.

(Step S61) The face feature value extraction region determination unit 192 acquires the face condition from the face condition table 185a.

(Step S62) The face feature value extraction region determination unit 192 determines the face feature value extraction region based on the extraction region determination model table 186a and the face condition. For example, when the face condition is "WEARING MASK", the face feature value extraction region determination unit 192 determines the glabella region as the face feature value extraction region. For example, when the face condition is "WEARING SUNGLASSES", the face feature value extraction region determination unit 192 determines the mouth region and the cheek region as the face feature value extraction regions. For example, when the face condition is "LIGHT APPLIED FROM LEFT", the face feature value extraction region determination unit 192 determines the glabella region, the mouth region and a right cheek region as the face feature value extraction regions. Put another way, the face feature value extraction region determination unit 192 does not set a left cheek region as a face feature value extraction region.

According to the second embodiment, even when the user is wearing an attached object, the state determination device 100a is capable of making the determination of the unawakened state by using an extractable face feature value extraction region. Further, even when light is applied to the user, the state determination device 100a is capable of making the determination of the unawakened state by using an extractable face feature value extraction region.

Features in the embodiments described above can be appropriately combined with each other.

DESCRIPTION OF REFERENCE CHARACTERS

10, 10a: extraction unit, 100, 100a: state determination device, 101: processor, 102: volatile storage device, 103: nonvolatile storage device, 104: camera, 105: display, 110: acquisition unit, 120: face region extraction unit, 130: face feature point extraction unit, 140: face feature value extraction region calculation unit, 150: face feature value extraction unit, 160: state determination unit, 170: output unit, 180: face feature point storage unit, 180a: face feature point table, 181: face feature value storage unit, 181a: face feature value table, 182: state determination model storage unit, 182a: state determination model table, 183: determination result storage unit, 183a: determination result table, 184: average face feature point model storage unit, 184a: average face feature point model table, 185: face condition storage unit, 185a: face condition table, 186: extraction region determination model storage unit, 186a: extraction region determination model table, 191: face condition judgment unit, 192: face feature value extraction region determination unit, 200: midpoint, 201: rectangular region, 210: midpoint, 211: rectangular region.

What is claimed is:

1. A state determination device comprising:
a processor to execute a program; and
a memory to store the program which, when executed by the processor, performs processes of,
extracting a face region representing a region corresponding to a face from each of a plurality of image frames successively obtained by electronically capturing images of a user's face, extracting face feature points representing parts of the face from the face region, calculating a face feature value extraction region as a region where a change occurs in the face region when the user is in an unawakened state based on the face feature points, extracting a face feature value as a feature value from the face feature value extraction region,
determining whether the user is in the unawakened state or not based on the face feature value in each of the plurality of frames and previously generated determination information, and outputting a determination result,
wherein
the face feature value extraction region is a mouth region in the face region,
the determination information includes information for determining an unawakenedness level according to a number of times the user licked the user's lips, and
when a process of the determining whether the user is in the unawakened state or not is executed, the program which, when executed by the processor, performs processes of,
calculating the number of times the user licked the lips based on the face feature value extracted from the mouth region in each of the plurality of frames, determining the unawakenedness level based on the number of times the user licked the lips and the determination information, and determining that the user is in the unawakened state when the determined unawakenedness level is higher than or equal to a predetermined threshold level, wherein the user is an automobile driver or a factory worker and the process of determining whether the user is in the unawakened state or not determines whether or not the automobile driver or factory worker is in the unawakened state to improve automotive or factory safety, respectively, and wherein the process of determining the unawakenedness level accesses a state determination model table stored in memory and compares the calculated number of times the user licked the lips with information stored in the state determination model.

2. The state determination device according to claim 1, wherein the determined unawakenedness level is output to indicate the unawakened state of the automobile driver or factory worker.

3. The state determination device according to claim 1, wherein
the face feature value extraction region is a glabella region and the mouth region in the face region,
the determination information includes information for determining an unawakenedness level according to a number of times the user wrinkled the user's glabella and information for determining an unawakenedness level according to a number of times the user licked the user lips, and
when a process of the determining whether the user is in the unawakened state or not is executed, the program which, when executed by the processor, performs processes of,
calculating the number of times the user wrinkled the glabella based on the face feature value extracted from the glabella region in each of the plurality of frames, determining the unawakenedness level based on the number of times the user wrinkled the glabella and the determination information, calculating the number of times the user licked the lips based on the face feature value extracted from the mouth region in each of the plurality of frames, determining the unawakenedness level based on the number of times the user licked the lips and the determination information, calculating a mean value of the determined unawakenedness levels, and determining that the user is in the unawakened state if the mean value is higher than or equal to a predetermined threshold value.

4. The state determination device according to claim 3, wherein information representing the mean value is output to indicate the unawakenedness state of the automobile driver or factory worker.

5. The state determination device according to claim 3, wherein
the program which, when executed by the processor, performs processes of,
judging whether the user is wearing an attached object or not based on the plurality of frames; and
determining the face feature value extraction region based on extraction region determination model information, indicating which region in the face region should be determined as the face feature value extraction region depending on a position where the attached object has been worn, when the user is judged to be wearing the attached object.

6. The state determination device according to claim 5, wherein
when a process of the judging whether the user is wearing an attached object or not is executed, the program which, when executed by the processor, performs a process of judging whether the user is wearing the attached object or not based on average face feature point model information indicating positions of parts of an average face and positions of the face feature points.

7. The state determination device according to claim 3, wherein
the program which, when executed by the processor, performs processes of,
judging whether or not a shadow or a color skip exists in any frame among the plurality of frames; and
determining the face feature value extraction region based on extraction region determination model information, indicating which region in the face region should be determined as the face feature value extraction region depending on a position where the shadow or the color skip exists, when the shadow or the color skip is judged to exist in any frame among the plurality of frames.

8. The state determination device according to claim 1, wherein
the face feature value extraction region is the mouth region and a cheek region in the face region,
the determination information includes information for determining an unawakenedness level according to a number of times the user licked the user's lips and information for determining an unawakenedness level according to a number of times the user yawned, and
when a process of the determining whether the user is in the unawakened state or not is executed, the program which, when executed by the processor, performs processes of,
calculating the number of times the user licked the lips based on the face feature value extracted from the mouth region in each of the plurality of frames, determining the unawakenedness level based on the number of times the user licked the lips and the determination information, calculating the number of times the user yawned based on the face feature values extracted from the mouth region and the cheek region in each of the plurality of frames, determining the unawakenedness level based on the number of times the user yawned and the determination information, calculating a mean value of the determined unawakenedness levels, and determining that the user is in the unawakened state if the mean value is higher than or equal to a predetermined threshold value.

9. The state determination device according to claim 1, wherein
the face feature value extraction region is a glabella region, the mouth region and a cheek region in the face region,
the determination information includes information for determining an unawakenedness level according to a number of times the user wrinkled the user's glabella, information for determining an unawakenedness level according to a number of times the user licked the user's lips, and information for determining an unawakenedness level according to a number of times the user yawned, and
when a process of the determining whether the user is in the unawakened state or not is executed, the program which, when executed by the processor, performs processes of, calculating the number of times the user wrinkled the glabella based on the face feature value extracted from the glabella region in each of the plurality of frames, determining the unawakenedness level based on the number of times the user wrinkled the glabella and the determination information, calculating the number of times the user licked the lips based on the face feature value extracted from the mouth region in each of the plurality of frames, determining the unawakenedness level based on the number of times the user licked the lips and the determination information, calculating the number of times the user yawned based on the face feature values extracted from the mouth region and the cheek region in each of the plurality of frames, determining the unawakenedness level based on the number of times the user yawned and the determination information, calculating a mean value of the determined unawakenedness levels, and determining that the user is in the unawakened state if the mean value is higher than or equal to a predetermined threshold value.

10. The state determination device according to claim 1, wherein the determination information is information obtained by means of machine learning and information for determining whether or not the user is in the unawakened state.

11. A state determination method performed by a state determination device, the state determination method comprising:
  extracting a face region representing a region corresponding to a face from each of a plurality of images frames successively obtained by electronically capturing images of a user's face, extracting face feature points representing parts of the face from the face region, calculating a face feature value extraction region as a region where a change occurs in the face region when the user is in an unawakened state based on the face feature points, extracting a face feature value as a feature value from the face feature value extraction region,
  determining whether the user is in the unawakened state or not based on the face feature value in each of the plurality of frames and previously generated determination information, and
  outputting a determination result,
  wherein
  the face feature value extraction region is a mouth region in the face region,
  the determination information includes information for determining an unawakenedness level according to a number of times the user licked the user's lips, and
  when the state determination device determines whether the user is in the unawakened state or not, the state determination method includes calculating the number of times the user licked the lips based on the face feature value extracted from the mouth region in each of the plurality of frames, determining the unawakenedness level based on the number of times the user licked the lips and the determination information, and determining that the user is in the unawakened state when the determined unawakenedness level is higher than or equal to a predetermined threshold level,
  wherein the user is an automobile driver or a factory worker and the process of determining whether the user is in the unawakened state or not determines whether or not the automobile driver or factory worker is in the unawakened state to improve automotive or factory safety, respectively, and
  wherein the process of determining the unawakenedness level accesses a state determination model table stored in memory and compares the calculated number of times the user licked the lips with information stored in the state determination model.

12. A non-transitory computer-readable recording medium storing a program for causing a processor of a state determination device to execute a process of:
  extracting a face region representing a region corresponding to a face from each of a plurality of image frames successively obtained by electronically capturing images of a user's face, extracting face feature points representing parts of the face from the face region, calculating a face feature value extraction region as a region where a change occurs in the face region when the user is in an unawakened state based on the face feature points, extracting a face feature value as a feature value from the face feature value extraction region,
  determining whether the user is in the unawakened state or not based on the face feature value in each of the plurality of frames and previously generated determination information, and
  outputting a determination result,
  wherein
  the face feature value extraction region is a mouth region in the face region,
  the determination information includes information for determining an unawakenedness level according to a number of times the user licked the user's lips, and
  when a process of the determining whether the user is in the unawakened state or not is executed, the program which, when executed by the processor, performs processes of,
  calculating the number of times the user licked the lips based on the face feature value extracted from the mouth region in each of the plurality of frames, determining the unawakenedness level based on the number of times the user licked the lips and the determination information, and determining that the user is in the unawakened state when the determined unawakenedness level is higher than or equal to a predetermined threshold level,
  wherein the user is an automobile driver or a factory worker and the process of determining whether the user is in the unawakened state or not determines whether or not the automobile driver or factory worker is in the unawakened state to improve automotive or factory safety, respectively, and
  wherein the process of determining the unawakenedness level accesses a state determination model table stored in memory and compares the calculated number of times the user licked the lips with information stored in the state determination model.

13. A state determination device comprising:
  a processor to execute a program; and
  a memory to store the program which, when executed by the processor, performs processes of,
  extracting a face region representing a region corresponding to a face from each of a plurality of image frames successively obtained by electronically capturing images of a user's face, extracting face feature points representing parts of the face from the face region, calculating a face feature value extraction region as a region where a change occurs in the face region when the user is in an unawakened state based on the face feature points, extracting a face feature value as a feature value from the face feature value extraction region, determining whether the user is in the unawakened state or not based on the face feature value in each of the plurality of frames and previously generated determination information, and outputting a determination result, wherein the face feature value extraction region is a glabella region, a mouth region and a cheek region in the face region, the determination information includes information for determining an unawakenedness level according to a number of times the user wrinkled the user's glabella and information for determining an unawakenedness level according to a number of times the user yawned, and when a process of the determining whether the user is in the unawakened state or not is executed, the program which, when executed by the processor, performs processes of, calculating the number of times the user wrinkled the glabella based on the face feature value extracted from the glabella region in each of the plurality of frames, determining the unawakenedness level based on the number of times the user wrinkled the glabella and the determination information, calculating the number of times the user yawned based on the face feature values extracted from the mouth region and the cheek region in each of the plurality of frames, determining the unawakenedness level based on the number of times the user yawned and the determination information, calculating a mean value of the determined unawakenedness levels, and determining that the user is in the unawakened state when the mean value is higher than or equal to a predetermined threshold value, wherein the user is an automobile driver or a factory worker and the process of determining whether the user is in the unawakened state or not determines whether or not the automobile driver or factory worker is in the unawakened state to improve automotive or factory safety, respectively, and wherein the process of determining the unawakenedness level accesses a state determination model table stored in memory and compares the calculated number of times the user wrinkled the glabella with information stored in the state determination model.

14. A state determination method performed by a state determination device, the state determination method comprising:

Extracting a face region representing a region corresponding to a face from each of a plurality of image frames successively obtained by electronically capturing images of a user's face, extracting face feature points representing parts of the face from the face region, calculating a face feature value extraction region as a region where a change occurs in the face region when the user is in an unawakened state based on the face feature points, extracting a face feature value as a feature value from the face feature value extraction region, determining whether the user is in the unawakened state or not based on the face feature value in each of the plurality of frames and previously generated determination information, and outputting a determination result, wherein the face feature value extraction region is a glabella region, a mouth region and a cheek region in the face region, the determination information includes information for determining an unawakenedness level according to a number of times the user wrinkled the user's glabella and information for determining an unawakenedness level according to a number of times the user yawned, and when the state determination device determines whether the user is in the unawakened state or not, the state determination method includes calculating the number of times the user wrinkled the glabella based on the face feature value extracted from the glabella region in each of the plurality of frames, determining the unawakenedness level based on the number of times the user wrinkled the glabella and the determination information, calculating the number of times the user yawned based on the face feature values extracted from the mouth region and the cheek region in each of the plurality of frames, determining the unawakenedness level based on the number of times the user yawned and the determination information, calculating a mean value of the determined unawakenedness levels, and determining that the user is in the unawakened state when the mean value is higher than or equal to a predetermined threshold value, wherein the user is an automobile driver or a factory worker and the process of determining whether the user is in the unawakened state or not determines whether or not the automobile driver or factory worker is in the unawakened state to improve automotive or factory safety, respectively, and wherein the process of determining the unawakenedness level accesses a state determination model table stored in memory and compares the calculated number of times the user wrinkled the glabella with information stored in the state determination model.

15. A non-transitory computer-readable recording medium storing a program for causing a processor of a state determination device to execute a process of:

extracting a face region representing a region corresponding to a face from each of a plurality of image frames successively obtained by electronically capturing images of a user's face, extracting face feature points representing parts of the face from the face region, calculating a face feature value extraction region as a region where a change occurs in the face region when the user is in an unawakened state based on the face feature points, extracting a face feature value as a feature value from the face feature value extraction region, determining whether the user is in the unawakened state or not based on the face feature value in each of the plurality of frames and previously generated determination information, and outputting a determination result, wherein the face feature value extraction region is a glabella region, a mouth region and a cheek region in the face region, the determination information includes information for determining an unawakenedness level according to a number of times the user wrinkled the user's glabella and information for determining an unawakenedness level according to a number of times the user yawned, and when a process of the determining whether the user is in the unawakened state or not is executed, the program which, when executed by the processor, performs processes of, calculating the number of times the user wrinkled the glabella based on the face feature value extracted from the glabella region in each of the plurality of frames, determining the unawakenedness level based on the number of times the user wrinkled the glabella and the determination information, calculating the number of times the user yawned based on the face feature values extracted from the mouth region and the cheek region in each of the plurality of frames, determining the unawakenedness level based on the number of times the user yawned and the determination information, calculating a mean value of the determined unawakenedness levels, and determining that the user is in the unawakened state when the mean value is higher than or equal to a predetermined threshold value, wherein the user is an automobile driver or a factory worker and the process of determining whether the user is in the unawakened state or not determines whether or not the automobile driver or factory worker is in the unawakened state to improve automotive or factory safety, respectively, and wherein the process of determining the unawakenedness level accesses a state determination model table stored in memory and compares the calculated number of times the user wrinkled the glabella with information stored in the state determination model.

* * * * *